United States Patent [19]

Newcomb

[11] 4,178,936

[45] Dec. 18, 1979

[54] APPARATUS FOR USE IN COLLECTING EGGS FROM ANIMALS

[75] Inventor: Raymond Newcomb, Sudbury, England

[73] Assignee: Milk Marketing Board, Surrey, England

[21] Appl. No.: 819,419

[22] Filed: Jul. 27, 1977

[30] Foreign Application Priority Data

Aug. 2, 1976 [GB] United Kingdom .............. 32184/76

[51] Int. Cl.² .......................................... A61M 25/00
[52] U.S. Cl. .............................. 128/349 B; 128/241; 128/348
[58] Field of Search ................... 128/349 B, 240, 241, 128/349, 350, 348, DIG. 26; 119/14.19

[56] References Cited

U.S. PATENT DOCUMENTS

| 3,394,705 | 7/1968 | Abramson | 128/241 X |
| 3,742,958 | 7/1973 | Rundles | 128/349 R X |
| 3,902,492 | 9/1975 | Greenbalgh | 128/241 |
| 4,004,588 | 1/1977 | Alexander | 128/241 |
| 4,016,509 | 8/1978 | McWaorter | 128/349 B |
| 4,077,412 | 3/1978 | Moosun | 128/347 |

Primary Examiner—Stephen C. Pellegrino
Attorney, Agent, or Firm—Armstrong, Nikaido, Marmelstein & Kubovcik

[57] ABSTRACT

In the collection of eggs (ova) from animals such as cows, a flexible catheter is introduced through a rigid external introducer, the catheter being provided with an inflatable cuff to seal off a uterine horn and with channel means for a flushing fluid.

8 Claims, 11 Drawing Figures

APPARATUS FOR USE IN COLLECTING EGGS FROM ANIMALS

BACKGROUND OF THE INVENTION

This invention relates to an apparatus for collecting eggs (ova) from animals. In the following description, much reference will be made to the collection of bovine ova but it is to be appreciated that the apparatus of the present invention, when constructed on an appropriate scale, can be used for the collection of ova from animals other than cows.

It is known to use for this purpose a three-way catheter equipped at some distance from its leading end with an inflatable cuff which, after being passed beyond the cervix, can be inflated by air introduced through one channel to seal the catheter within one uterine horn. Flushing fluid can then be introduced through a second channel, to emerge at the leading end region of the catheter, which fluid flushes out eggs. The flushing fluid with eggs therein can then pass through an aperture immediately ahead of the inflated cuff, to a third channel from which the eggs may be recovered.

Whilst the catheter is being passed through the cervix, the catheter can be made rigid by the presence in the largest of its three channels of a rigid stylet, which is removed prior to the introduction of fluid through the second channel.

SUMMARY OF THE INVENTION

According to one aspect of the present invention, there is provided an apparatus for collecting eggs from an animal, which apparatus comprises:

(i) a generally rigid tubular member open at both ends, and (ii) a catheter comprising (a) a tubular portion provided over at least part of its length with a plurality of internal channels, (b) a rigid head portion provided at one end of the tubular portion, and (c) an inflatable cuff provided on the outside of an intermediate region of the tubular portion, wherein a first channel within the tubular portion communicates with at least one outwardly opening hole in the head portion, a second channel within the tubular portion communicates with at least one outwardly opening hole in the tubular portion in a region between the inflatable cuff and the head portion, and a third channel within the tubular portion communicates with the interior of the inflatable cuff; and wherein the tubular portion and cuff, when non-inflated, are slidable within the rigid tubular member, and the head portion, when abutting the rigid tubular member, forms with the leading end region of the rigid tubular member a generally smooth, rounded leading end region to the apparatus. This apparatus will hereinafter be referred to as "the first aspect apparatus".

The head portion (b) of the catheter of the first aspect apparatus can be formed of, for example, stainless steel or a synthetic plastics material. Conveniently the tubular portion (a) is formed of a polyvinyl chloride and the cuff (c) of latex.

Conveniently that end of the rigid tubular member (i) which is to be inserted in the animal is bevelled, and a trailing part of the head portion (b) can be of reduced diameter and can fit within the bevelled end region of the rigid tubular member. The opposite end region of the rigid tubular member (i) can be provided with a handle, and the catheter (ii) is longer than the rigid tubular member so that those regions of the catheter outside the trailing end of the rigid tubular member (i) can be pushed into that member to cause the catheter to project well beyond the leading end of the rigid tubular member (i).

The apparatus can also include a plastic sheath intended to enclose both the rigid tubular member (i) and the head portion (a) of the catheter (ii) when the head portion abuts the leading end of the rigid tubular member. The purpose of the sheath is to preserve sterile conditions for the head portion and leading end of the rigid tubular member during passage through the animal's vagina until the cervix is approached, whereupon the sheath can be ruptured and the tubular member and head portion passed through the cervix into a uterine horn.

The flexible tubular portion can be, for instance, a single elongate body provided with three channels; another possibility is for the flexible tubular portion to be constituted by a first tube in the channel of which are second and third tubes each with their own channel.

The tubular portion should be sufficiently flexible to follow the curve of the uterine horn, but should nonetheless have sufficient rigidity to allow itself to be fed through the tubular member and along the uterine horn.

It is envisaged that the rigid head portion (b) of the catheter of the first aspect apparatus will have an overall diameter greater than that of the tubular portion (a) of the catheter. This, however, can present some difficulties during construction of the catheter (particularly if the head portion is formed of a different material) and, therefore, attention has been given to the possibility of making the leading region of the tubular portion of the same diameter as the rest of the tubular portion, with a view to simplifying construction of the catheter. In such a case, however, it appears desirable to modify the means for introducing the catheter; in fact, it is recommended to replace the generally rigid tubular member open at both ends by an introducer comprising (a) a generally rigid tubular outer member open at both ends, and (b) an inner member locatable within the outer member and provided over its length with a duct. The arrangement of the introducer is such that, in use, the introducer, with the inner member located appropriately within the outer member, can be passed through the cervix of the animal, and any mucus can be withdrawn by suction through the duct in the inner member. After this, whilst leaving the outer member in place within the cervix, the inner member can be withdrawn and the catheter can then be passed through the outer member of the introducer.

Thus, according to a second aspect of the present invention, there is provided an apparatus for collecting eggs from an animal, which apparatus comprises:

(i) an introducer comprising (a) a generally rigid tubular outer member open at both ends, and (b) an inner member locatable within the outer member and provided over its length with a duct; and (ii) a catheter comprising (a) a tubular portion provided over at least part of its length with a plurality of internal channels and terminating at one end in a leading region, and (b) an inflatable cuff provided on the outside of an intermediate region of the tubular portion, wherein a first channel within the tubular portion communicates with at least one outwardly opening hole in the leading region, a second channel within the tubular portion communicates with at least one outwardly opening hole in the tubular portion in a region between the inflatable cuff and the leading region; and a third channel within the tubular portion communicates with the interior of the inflatable cuff; wherein the tubular portion and cuff, when non-inflated, are slidable within the rigid tubular outer member of the introducer; and wherein, when the inner member is within the outer member, the leading end region of the introducer is generally smooth; the arrangement being such that, in use, the introducer is passed through the cervix of the animal with the inner member within the outer member, after which the inner member is withdrawn and the catheter is introduced into the outer member until the cuff has passed beyond the outer member, whereupon the cuff is inflated and fluid introduced through the first channel. This apparatus will hereinafter be referred to as "the second aspect apparatus".

Conveniently the tubular portion (a) is formed of a polyvinyl chloride and the cuff (b) of latex, in the second apparatus.

In the second aspect apparatus defined above, the catheter is provided with three channels, the first of which is for the introduction of flushing fluid to the leading region of the catheter, the second of which is to permit the flushing fluid (with eggs entrained) to be withdrawn through the catheter, and the third of which is to allow for the introduction of air into the inflatable cuff so as to inflate the cuff once the leading end region of the catheter is correctly positioned within the uterine horn. The second aspect apparatus is intended to be used in a manner such that, during use, with the catheter correctly located within the uterine horn, flushing fluid is passed through the first channel, emerges at the leading region of the catheter, entrains eggs, re-enters the catheter through the hole or holes between the inflatable cuff and the leading region, and passes back through the second channel. An alternative arrangement is that wherein the second channel is dispensed with, and the fluid flow through the first channel is reversible, so that fluid is passed through the catheter in one direction into the uterine horn and then the flow of fluid is reversed so that the fluid, as well as eggs entrained therein, are conducted back through the same first channel to the exterior. The fluid flow in such a case can be regarded as tidal.

Thus, according to a third aspect of the present invention, there is provided an apparatus for collecting eggs from an animal, which apparatus comprises:

(i) an introducer comprising (a) a generally rigid tubular outer member open at both ends, and (b) an inner member locatable within the outer member and provided over its length with a duct; and (ii) a catheter comprising (a) a tubular portion provided over at least part of its length with a plurality of internal channels and terminating at one end in a leading region, and (b) an inflatable cuff provided on the outside of an intermediate region of the tubular portion, wherein a first channel within the tubular portion communicates with at least one outwardly opening hole in the leading region, and a second channel within the tubular portion communicates with the interior of the inflatable cuff; wherein the tubular portion and cuff, when non-inflated, are slidable within the rigid tubular outer member of the introducer; and wherein, when the inner member is within the outer member, the leading end region of the introducer is generally smooth; the arrangement being such that, in use, the introducer is passed through the cervix of the animal with the inner member within the outer member, after which the inner member is withdrawn and the catheter is introduced into the outer member until the cuff has passed beyond the outer member, whereupon the cuff is inflated and the fluid introduced through the first channel. This apparatus will hereinafter be referred to as "the third aspect apparatus".

Conveniently the tubular portion (a) is formed of a polyvinyl chloride and the cuff (b) of latex, in the third aspect apparatus.

As with the first aspect apparatus, the second and third aspect apparatuses can also include a plastic sheath intended to enclose the introducer as the introducer is passed through the vagina of the animal. When the cervix is approached, the sheath can be ruptured and the introducer (both the outer member and the inner member), can be passed through the cervix into the uterine horn.

As with the first aspect apparatus, the flexible tubular portion of the catheter of the second aspect apparatus can be, for instance, a single elongate body provided with three channels; alternatively the flexible tubular portion can be constituted by a first tube in the channel of which are second and third tubes each with their own channel. Similarly, with regard to the third aspect apparatus, the tubular portion of the catheter can be a single elongate body provided with two channels, or can be constituted by a first tube in the channel of which is a second tube with its own channel.

Preferably the leading part of the catheter is, when unrestrained, slightly angled, which is intended to permit the catheter to follow more easily the path of the uterine horn. Also, generally the catheter has a slight curve such that the openings (for fluid collection) in the catheter remain in that part of the tubular member furthest from that wall of the uterine horn having the greatest radius of curvature, thereby preventing these openings from becoming blocked.

In the catheter of the second aspect apparatus, when the tubular portion is constituted by a single elongate body provided with three channels, the leading end region of the tubular portion of the catheter can be fused in a manner such that two of the channels are blocked, leaving clear only the first channel to permit flushing fluid to be discharged from the leading end of the catheter. Alternatively, instead of fusing the tubular portion in the region of the two other channels, the leading end region of the catheter can be cut and some suitable material introduced into the second and third channels in the region of the leading end in order to block those channels, again leaving clear only the first channel.

In the case in which the tubular portion of the catheter is constituted by a single elongate body provided with two or three channels, these channels can communicate at a trailing end region of the tubular portion with smaller tubes associated with (i) means for supplying the flushing fluid, (ii) means for collecting flushing fluid discharged at the trailing end of the catheter, and (iii) means for supplying air under pressure in order to inflate the catheter.

The introducer per se which forms part of the second and third aspect apparatuses, also constitutes a further aspect of the present apparatus.

DESCRIPTION OF THE DRAWINGS

For a better understanding of the present invention, and to show how the same may be carried into effect, reference will now be made, by way of example, to the accompanying drawings, in which.

Figure 1:
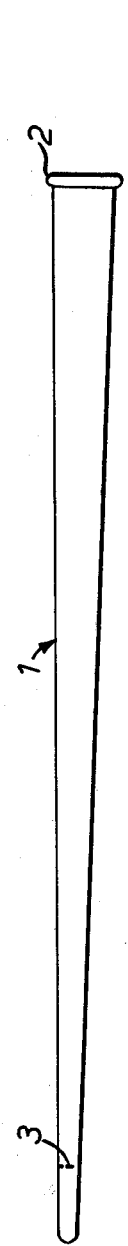
FIG. 1 is a side view of a sheath forming part of one embodiment of the first aspect apparatus according to the present invention.

Referring firstly to FIG. 1, the sheath is formed for the most part of a thin plastics material 1 tapering over its whole length. At one end is a rigid ring 2 and near the opposite end is a series of perforations 3 extending approximately three quarters of the way around the periphery.

Figure 2:
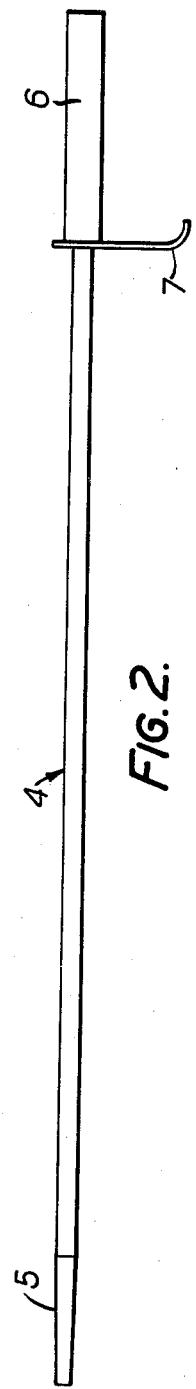
FIG. 2 is a side view of the rigid tubular member forming part of the same embodiment.

FIG. 2 shows the rigid tubular member generally indicated by the reference numeral 4 which tapers at one end region 5 and is provided at its opposite end region with a handle 6 and guard 7. The tubular member is formed of stainless steel.

Figure 3:
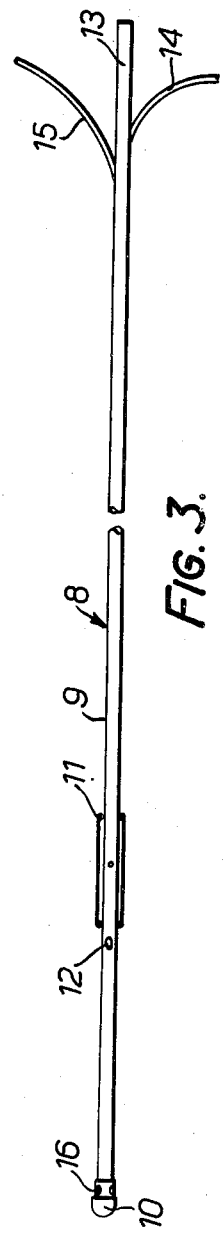
FIG. 3 is a side view of the catheter forming part of the same embodiment.
Figure 4:
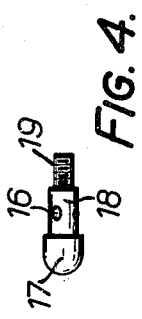
FIG. 4 is a side view, on an enlarged scale of the head portion of the catheter shown in FIG. 3.

FIG. 3 shows the catheter generally indicated by the reference numeral 8, having a synthetic plastics tubular portion 9 provided with three internal channels (not shown). At one end of the tubular portion 9 is a stainless steel head portion 10 shown in more detail in FIG. 4. At an intermediate position along the outside of the tubular portion 9 is an inflatable cuff 11, and near the cuff 11 but on that side thereof nearer the head portion 10 is a collection hole 12 in the tubular portion 9.

At that end region 13 of the tubular portion 9 remote from the head portion 10 is a pipe 14 for introducing air into one channel in the tubular portion 9, which channel communicates via a hole in the tubular portion 9 with the interior of the cuff 11.

Also in region 13 is a pipe 15 for introducing flushing fluid into a second channel in the tubular portion 9, which channel communicates with holes 16 in the head portion 10.

The hole 12 communicates with a third channel in the tubular portion 9, which channel opens at the free end of the tubular portion 9.

The head portion 10 has a rounded leading region 17, and intermediate region 18 of reduced diameter relative to the maximum diameter of region 17, and a trailing region 19 of even less diameter. It is the intermediate region 18 which is provided with three holes 16. The trailing region 19 is provided with a tapped surface region for screwing into the leading end region of the tubular portion 9.

The method of using the illustrated apparatus will now be described.

Within the outer plastic sheath (shown in FIG. 1) is the rigid tubular member 4 within which is the catheter 8. The intermediate region 18 of the head portion 10 fits snugly within the leading end of the tubular member 4 so that, with the stainless steel head portion 10, there is provided a rounded all metal appearance.

The method of use of the previously sterilised equipment is to pass the apparatus through the vagina of the animal using the rectal technique and then at the entrance of the animal's cervix to retract the outer plastic sheath so that the metal tubular member 4 and head portion 10 protrude from it. The tubular member is then passed through the animal's cervix to just within the uterine horn, and then the catheter is advanced around the uterus and guided as far as possible towards the uterotubal junction. The cuff 11 is then inflated with 10 ml approx. of air via pipe 14. A small quantity of flushing fluid is passed along the outlet channel to ensure that the outlet hole 12 is not blocked with mucus. The flushing fluid is sent through the inlet channel via pipe 15 and holes 16, and collected immediately anterior to the inflated cuff 11 and passed to a collection vessel at the outlet point. This fluid is then examined for the presence of an egg(s).

There will now be given, purely by way of exemplification, suitable dimensions for the illustrated apparatus when the latter is to be used to collect eggs from cows, it being appreciated that the eggs are of the order to magnitude of a speck of cigarette ash and that the apparatus can be appropriately dimensioned for use with other animals.

The rigid tubular member has a length of 15 inches from the tapered end 5 to the guard 7, and the nylon handle 6 has a length of 3 inches with an external diameter of 0.5 inch. The tapered region 5 has a degree of taper of 0.05° which extends over 1.625 inch. The tubular member has an external diameter of 0.25 inch and is formed of 22 S.W.G. stainless steel.

The sheath has an overall length of 14 inches, with the ring 2 having a diameter of 1 inch. The sheath tapers to a diameter of 0.25 inch at its narrow end, and the perforations 3 are about 1 inch from the narrow end.

The tubular portion 9 of the catheter 8 has a length of 36 inches, the air pipe 14 entering 2.5 inches from the trailing end and the fluid inlet pipe 15 entering 3.5 inches from that end. The collection hole 12 is 6 inches from the leading end of tubular portion 9, the cuff 11 has a length of 1 inch and the airhole communicating with the interior of the cuff 11 is 6.5 inches from the leading end of portion 9. The air hole has a diameter of 0.75 mm. The collection hole 12 is oval and has a maximum length of 0.140 inch and a maximum width of 0.080 inch.

The head portion 10 projects about 0.420 inch beyond the tubular portion 9. The region 17 has a length of 0.260 inch, region 18 a length of 0.160 and region 19 a length of 0.230 inch.

Figure 5:
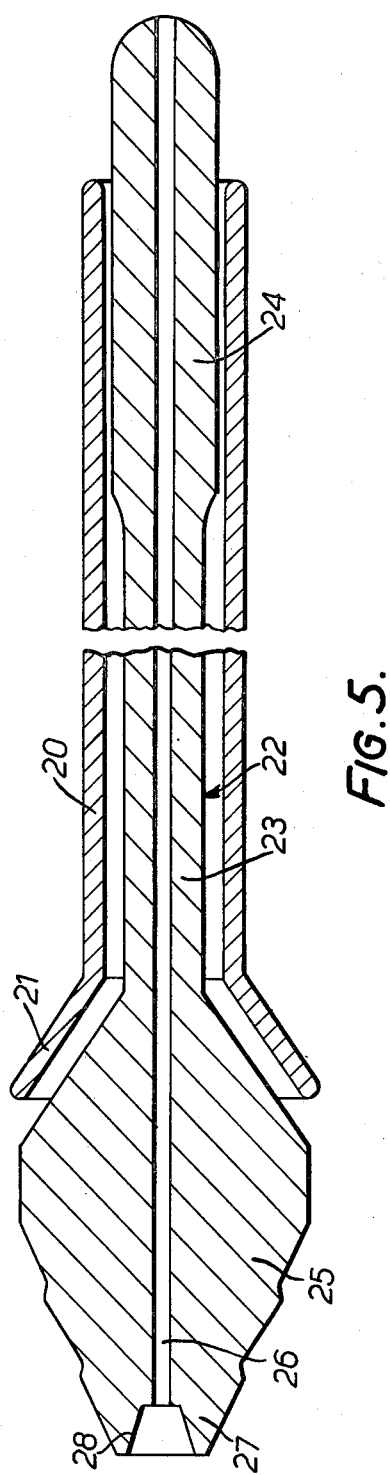
FIG. 5 is a longitudinal section through an introducer forming part of one embodiment of a second or third aspect apparatus according to the present invention.

Referring now to FIG. 5 of the accompanying drawings, the illustrated introducer comprises an outer member 20 which is cylindrical over the majority of its length, apart from an outwardly flaring trailing end region 21. Shown located within the outer member 20 is an inner member generally indicated by the reference 22, which has a generally cylindrical intermediate region 23, a leading region 24 of increased external diameter, and a trailing region 25 also of increased diameter. Extending along the axis of the inner member 22 is a duct 26. The leading ends of both the outer member 20, and the leading region 24 of the inner member 22 are curved and smoothly shaped, with a view to reducing the likelihood of catching on any tissue within the animal.

The trailing end region 27 of the trailing region 25 of the inner member 22 is provided with a female luer 28 and is generally of such a shape that vacuum equipment can be releasably secured in an air-tight manner to the trailing region 25 with a view to clearing mucus through the duct 26 once the introducer (outer member 20 and inner member 22) has been passed through the cervix.

In practice, in use of the introducer illustrated in FIG. 5, the inner member 22 is located within the outer member 20 in the manner illustrated in FIG. 5 and thereafter the introducer, within a sterilized plastic sheath, is passed in through the vagina until the cervix is approached. Thereafter the sheath is ruptured and the whole introducer is advanced through the cervix, whereupon any mucus is withdrawn by vacuum action through the duct 26, after which the inner member 22 is withdrawn, leaving the outer member 20 in place. The catheter forming part of the second or third aspect apparatus is then fed through the outer member 20 until the leading end region of the catheter is estimated to be in the desired position, after which the inflatable cuff of the catheter is inflated and fluid is introduced through the catheter into the uterine horn to flush out the eggs. More details of the various types of catheter are given further below.

There will now be given, merely by way of example, an illustration of suitable dimensions for an introducer as shown in FIG. 5 when intended to be used for the recovery of eggs from a cow. The generally cylindrical portion of the outer member 20 is 18 inches in length and the length (measured axially) of the flared region 21 is 0.5 inch. The external diameter of the outer member 20 is 0.290 inch; the outer member 20 is formed of a metal or a plastics material. The overall length of the inner member 22 is 21.25 inches and, during introduction, the leading end region of the inner member 22 projects beyond the leading end of the outer member 20 by one inch. The leading region 24 has a length of 3 inches and has an external diameter of 0.235 inch, whereas the intermediate portion 23 has a length of 16 inches and an external diamter of 0.190 inch. The trailing region 25 has a maximum external diameter of 0.75 inch and an overall length of 2.25 inches.

Figure 6:
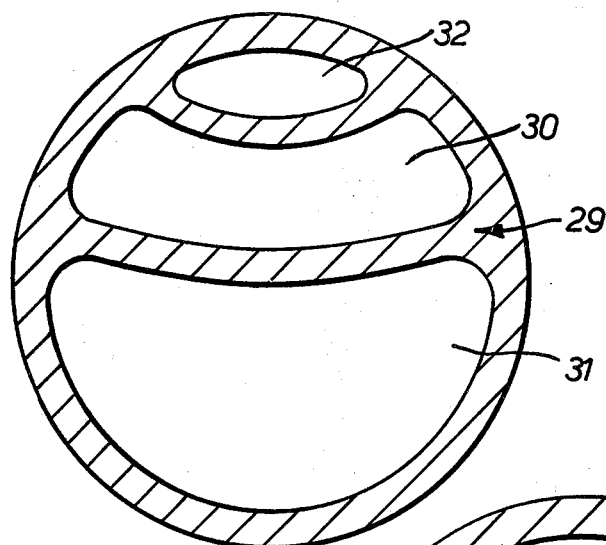
FIG. 6 is a cross-section through a tubular portion forming part of the catheter of one embodiment of the first or second aspect apparatus according to the present invention.

FIG. 6 illustrates a cross-section through the tubular portion of a preferred embodiment of a catheter forming part of the first or second aspect apparatus of the present invention. The tubular portion is generally indicated by the reference numeral 29 and is formed of a single elongate body provided with three channels, namely a first channel 30 for introducing fluid into the uterine horn, a second channel 31 for allowing flushing fluid to be removed from the uterine horn, and a third channel 32 for passing air to the inflatable cuff (such as the cuff 11 shown in FIG. 3). Where the catheter of the second aspect apparatus is produced from a single extrudate, the particular configuration of channels illustrated in FIG. 6 allows the fluid inlet hole 16 (in FIG. 3) to be positioned at the extremity of the catheter, and induces a natural bend in the tubular portion of the catheter, which may, for example, be formed as a polyvinyl chloride extrudate, to ensure that the fluid collection hole 12 was always positioned on the inside of this bend, thereby tending to prevent any occlusion of the hole with the endometrium.

Figure 7:
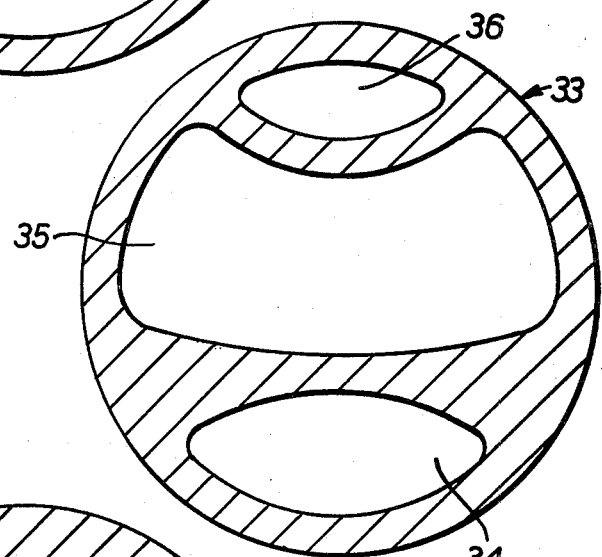
FIG. 7 is a cross-section through a different tubular portion of another catheter forming part of a different embodiment of a first or second aspect apparatus according to the present invention.
Figure 8:
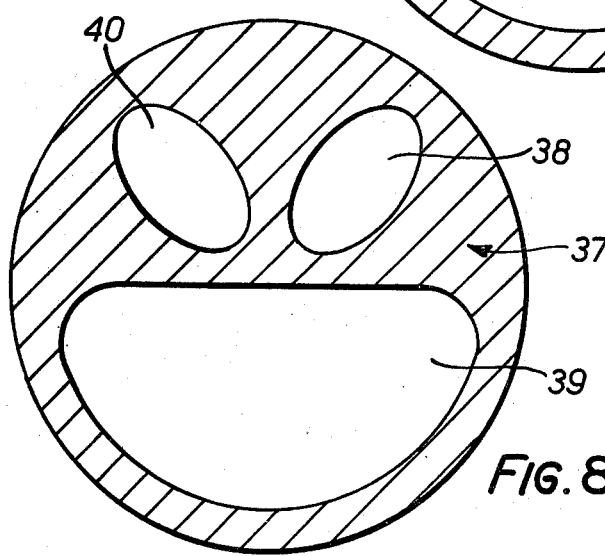
FIG. 8 is a cross-section through a further tubular portion of a different catheter forming part of a further embodiment of a first or second aspect apparatus of the present invention.

Alternative embodiments for the tubular portion of the catheter are illustrated in FIGS. 7 and 8 respectively. In FIG. 7, the tubular portion is shown generally by the reference numeral 33 and is provided with a first channel 34 for introducing flushing fluid, a second channel 35 as an outlet for the flushing fluid (with eggs entrained), and a third channel 36 for air to inflate the cuff. In the embodiment illustrated in FIG. 8 the single elongate body is indicated by the reference numeral 37 and is provided with three channels, namely a first channel 38 for introducing flushing fluid, a second channel 39 for removing the flushing fluid, and a third channel 40 for introducing air to inflate the cuff.

It will be appreciated from FIGS. 6, 7 and 8, that generally the largest channel is that for allowing the removal of the flushing fluid with eggs entrained and that the smallest channel is generally the inlet channel for the air (to inflate the cuff).

Figure 9:
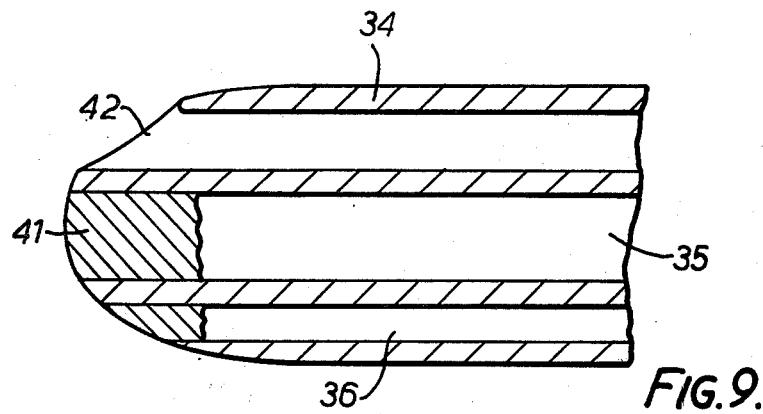
FIG. 9 is a longitudinal section through the leading end region of a catheter of one embodiment of the second aspect apparatus of the present invention.

FIG. 9 illustrates one arrangement for the leading end region of the catheter of the second aspect apparatus, this being similar to the arrangement shown in FIG. 7, but inverted. The same three channels 34, 35 and 36 are shown in FIG. 9 and it can be seen that the fluid inlet channel 34 opens at 42 in the region of the leading end of the catheter whereas the two other channels, 35 and 36, are sealed off by a fused region 41, with the result that the only channel which opens at the leading end region of the catheter is the fluid inlet channel 34.

Figure 10:
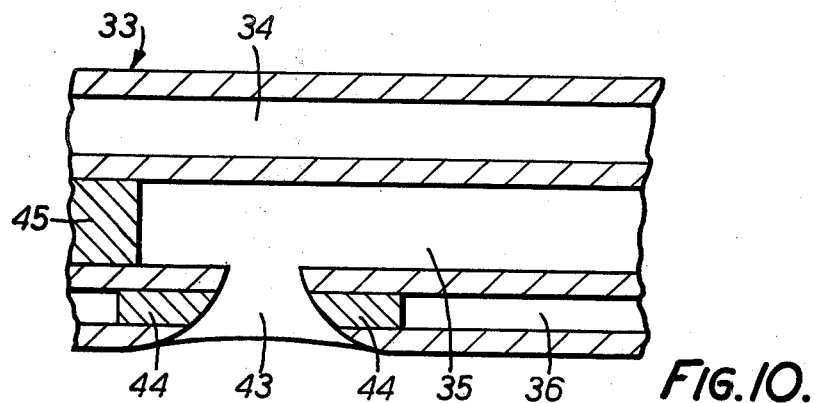
FIG. 10 is a longitudinal section through an intermediate region of the catheter of the same embodiment of the second aspect apparatus.

An intermediate region of the same catheter is shown in FIG. 10, this being a region immediately ahead of the cuff (not shown in FIG. 10). Here, the same three channels 34, 35 and 36 are shown (these being the same as for FIGS. 7 and 9). The wall of the body 33 is cut in a manner such that an opening 43 is formed which communicates with the fluid outlet channel 35. In order to avoid communication with the air inlet channel 36, adjacent regions 44 of that channel are blocked with a suitable sealing material. Similarly, that region 45 of the fluid outlet channel 35, on that side of the opening 43 nearer the leading end of the catheter, is also blocked.

Figure 11:
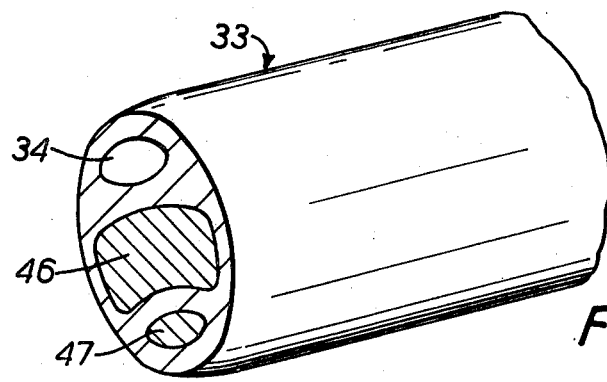
FIG. 11 is an oblique view of the leading end region of a different catheter forming part of a different embodiment of the second aspect apparatus according to the present invention.

FIG. 11 shows an alternative arrangement to that illustrated in FIG. 9. The body 33 has been cut and, instead of employing a fusing technique to seal the channels 35 and 36 (as shown in FIG. 9), the channel 35 is sealed with material 46 introduced into the leading end of that channel, and the channel 36 is sealed with material 47 introduced into the leading end of that channel.

The method of operation of the first aspect apparatus has already been described in detail and the same general technique applies with regard to the second aspect apparatus, apart from the different technique insofar as the introducer is concerned. With regard to the third aspect apparatus, the introduction of the catheter using the introducer can be effected in the same manner as with the second aspect apparatus. However, once the catheter is in position, and after the cuff has been inflated, instead merely of introducing the flushing fluid through one channel and removing it through a different channel, it is necessary to employ a "tidal" effect with the flushing fluid, whereby the flushing fluid is introduced through one channel is given the opportunity to entrain eggs and is then withdrawn through the same channel.

Mention was made earlier herein of the possibility of attaching pipes to the channels within the single elongate body forming the tubular portion of the catheter, and this technique is known in itself and no further elaboration on this point is therefore considered necessary. These pipes can be fitted with coupling members to enable the pipes to be fitted to the appropriate fluid or air sources.

In use of the first aspect apparatus, the head portion of the catheter abuts the leading end region of the tubular member and the resulting apparatus is enclosed in a sheath formed of plastics material. The sheath and apparatus are introduced through the vagina until the cervix is approached, whereupon the sheath is ruptured and the tubular member and head portion passed through the cervix into a uterine horn. The catheter is advanced sufficiently until the leading end of the catheter is, say, 1.5 inches from the utero-tubal junction, whereupon air is introduced through the third channel in order to inflate the cuff. Flushing fluid is then introduced through the first channel and into the uterine horn via the hole or holes in the head portion; the fluid, with any eggs entrained therein, then passes via the collection hole immediately ahead of the cuff and is recovered via the second channel. There is thus a close similarity between the method of operation of the first aspect apparatus and that of the second aspect apparatus.

As indicated above with regard to the first aspect apparatus, the leading end of the catheter is brought to approximately 1.5 inches from the utero-tubal junction before the cuff is inflated the the fluid introduced. In contrast, in the case of the third aspect apparatus (which has only the two channels), the single hole for the fluid through which the fluid is to be discharged and collected during the tidal action is preferably about 0.75 inch from the leading end of the catheter and the hole can be spaced approximately 0.25 inch ahead of the inflatable cuff which itself can have a length (measured in the axial direction) of 1.5 inches. With such a catheter of the third aspect apparatus, the leading end of the catheter is brought to about 6 inches from the utero-tubal junction before inflation of the cuff.

In much the same way as it is possible to modify the second aspect apparatus by replacing the three-channel catheter by a two-channel catheter to produce the third aspect apparatus, so it is also possible to modify the first aspect apparatus by replacing the three-channel catheter by a two-channel catheter, which results in an apparatus which will hereinafter be referred to as the "fourth aspect apparatus".

Insofar as they are applicable, the details given hereinabove in relation to the first aspect apparatus can also be related to the fourth aspect apparatus.

When a sheath is used for introducing the apparatus into the animal from which the eggs are to be collected, the sheath can, for example, be of the type shown in, and described with reference to, FIG. 1 of the accompanying drawings. Alternatively, the sheath, instead of being provided with a ring at the trailing end and with peripheral perforations near the leading end, can be provided with perforations which run along the longitudinal length of the sheath so that, when the times comes to advance the apparatus beyond the sheath, the sheath can be broken along the line of perforations and readily withdrawn from the animal, without so great a risk of leaving any of the material of the sheath within the animal.

I claim:

1. An apparatus for collecting eggs from the upper reaches of the uterine horn of an animal, which apparatus comprises:
    (i) an introducer comprising (a) a generally rigid tubular outer member open at both ends and having a smooth leading end region, and (b) an inner member locatable within the outer member and provided over its length with a duct, the inner member having a smooth leading end region; and
    (ii) a catheter of greater length than the introducer and comprising (a) a flexible tubular portion provided over at least part of its length with a plurality of internal channels and terminating at one end in a leading region, and (b) an inflatable cuff provided on the outside of an intermediate region of the tubular portion; wherein a first channel within the tubular portion communicates with at least one outwardly opening hole in the leading region, a second channel within the tubular portion communicates with at least one outwardly opening hole in the tubular portion in a region between the inflatable cuff and the leading region; and a third channel within the tubular portion communicates with the interior of the inflatable cuff; wherein the tubular portion and cuff, when non-inflated, are slidable within the rigid tubular outer member of the introducer; and wherein, when the inner member is within the outer member with the leading end of the inner member projecting slightly beyond that of the outer member, the leading end region of the introducer is generally smooth such that the leading end region of the introducer can be passed through the cervix of the animal without snagging any tissue; the arrangement being such that, in use, the leading region of the introducer is passed through the cervix of the animal with the inner member within the outer member, after which mucous may be withdrawn through the duct of the inner member, the inner member is withdrawn from the outer member, and the catheter is introduced into the outer member until the cuff has passed beyond the outer member, the flexibility of the catheter permitting the catheter to follow the curve of the uterine horn, whereupon, once the leading end region of the catheter is in the desired position, the cuff is inflated and fluid introduced through the first channel.

2. An apparatus according to claim 1, wherein the tubular portion is formed of a polyvinyl chloride and the cuff of latex.

3. An apparatus according to claim 1, wherein the tubular portion is selected from the group consisting of (a) a single elongate body provided with three channels, and (b) a first tube in the channel of which are second and third tubes each with their own channel.

4. An apparatus according to claim 1, wherein at the leading end region of the tubular portion of the catheter, each channel other than said first channel is blocked by the introduction of sealing material or by fusing.

5. An apparatus according to claim 1, wherein the leading end region of the catheter is, when unrestrained, slightly angled to assist the catheter to follow the path of the uterine horn, and the catheter is slightly curved.

6. An apparatus for collecting eggs from the upper reaches of the uterine horn of an animal, which apparatus comprises:
   (i) an introducer comprising (a) a generally rigid tubular outer member open at both ends and having a smooth leading end region, and (b) an inner member locatable within the outer member and provided over its length with a duct, the inner member having a smooth leading end region; and
   (ii) a catheter of greater length than the introducer and comprising (a) a flexible tubular portion provided over at least part of its length with a plurality of internal channels and terminating at one end in a leading region, and (b) an inflatable cuff provided on the outside of an intermediate region of the tubular portion; wherein a first channel within the tubular portion communicates with at least one outwardly opening hole in the leading region, and a second channel within the tubular portion communicates with the interior of the inflatable cuff; wherein the tubular portion and cuff, when non-inflated, are slidable within the rigid tubular outer member of the introducer; and wherein, when the inner member is within the outer member, with the leading end of the inner member projecting slightly beyond that of the outer member, the leading end region of the introducer is generally smooth such that the leading end region of the introducer can be passed through the cervix of the animal without snagging; the arrangement being such that, in use, the leading end region of the introducer is passed through the cervix of the animal with the inner member within the outer member, after which mucous may be withdrawn through the duct of the inner member, the inner member is withdrawn from the outer member, and the catheter is introduced into the outer member until the cuff has passed beyond the outer member, the flexibility of the catheter to follow the curve of the uterine horn, whereupon, once the leading end region of the catheter is in the desired position, the cuff is inflated and the fluid introduced through the first channel.

7. An apparatus according to claim 6, wherein the tubular portion is formed of a polyvinyl chloride and the cuff is latex.

8. An apparatus according to claim 6, wherein the leading end region of the catheter is, when unrestrained, slightly angled to assist the catheter to follow the path of the uterine horn, and the catheter is slightly curved.

* * * * *